(12) United States Patent
Kakizawa et al.

(10) Patent No.: US 8,298,585 B2
(45) Date of Patent: Oct. 30, 2012

(54) CELLULOSE-BASED FINE CORE PARTICLE AND PROCESS FOR PRODUCING THE SAME

(75) Inventors: Masayuki Kakizawa, Tokyo (JP); Hidetoshi Tomiyama, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 233 days.

(21) Appl. No.: 12/602,785

(22) PCT Filed: Jun. 4, 2008

(86) PCT No.: PCT/JP2008/060279

§ 371 (c)(1),
(2), (4) Date: Dec. 3, 2009

(87) PCT Pub. No.: WO2008/149894

PCT Pub. Date: Dec. 11, 2008

(65) Prior Publication Data

US 2010/0178332 A1    Jul. 15, 2010

(30) Foreign Application Priority Data

Jun. 6, 2007  (JP) ................................ 2007-150003

(51) Int. Cl.
*A61K 9/14*    (2006.01)
(52) U.S. Cl. ......... 424/489; 424/464; 424/474; 424/490
(58) Field of Classification Search ........................ None
See application file for complete search history.

(56) References Cited

U.S. PATENT DOCUMENTS

| | | | |
|---|---|---|---|
| 4,806,361 | A | 2/1989 | Harrison et al. |
| 5,384,130 | A | 1/1995 | Kamada |
| 5,997,905 | A | 12/1999 | McTeigue et al. |

FOREIGN PATENT DOCUMENTS

| | | |
|---|---|---|
| EP | 1 338 288 A1 | 8/2003 |
| JP | 61-001614 | 1/1986 |
| JP | 61-213201 | 9/1986 |
| JP | 07-002761 | 1/1995 |
| JP | 2542122 | 7/1996 |
| JP | 10-192687 | 7/1998 |
| JP | 2000-034224 | 2/2000 |
| JP | 2000-109426 | 4/2000 |
| JP | 2001-172430 | 6/2001 |
| JP | 2001172430 * | 6/2001 |
| WO | 02/36168 A1 | 5/2002 |

OTHER PUBLICATIONS

International Search Report for PCT/JP2008/060279, mailed Jul. 15, 2008.
International Preliminary Report on Patentability for PCT/JP2008/060279, mailed Dec. 15, 2009.

\* cited by examiner

*Primary Examiner* — Anand Desai
*Assistant Examiner* — Melissa Mercier
(74) *Attorney, Agent, or Firm* — Greenblum & Bernstein, P.L.C.

(57) ABSTRACT

It is an object of the present invention to provide a fine core particle, which comprises a coating layer having a uniform thickness, and which can be used to produce, at a high yield, a small granule causing no sandy feeling in the oral cavity when the fine core particle is applied to a fine granule or an orally-disintegrating tablet. According to the present invention, there is provided a core particle, which comprises 50% by mass or more of microcrystalline cellulose, and which has a mean particle diameter of less than 100 μm, a relative flow index of 7.0 to 30.0, a specific surface area of less than 0.15 $m^2/g$, and a tapped bulk density of 0.80 g/mL or more.

13 Claims, No Drawings

CELLULOSE-BASED FINE CORE PARTICLE AND PROCESS FOR PRODUCING THE SAME

TECHNICAL FIELD

The present invention relates to a core particle used in the production of a granule, a granule prepared using the core particle, and a tablet or a capsule comprising the granule.

BACKGROUND ART

As a method for preparing granules in the field of powder production of pharmaceutical products, food products, and the like, a method of coating a core particle with a coating layer according to a layering method has been known.

The term "layering method" used herein refers to a method of coating a core particle with a coating layer, which comprises spraying a layering liquid containing an active ingredient such as a medicinal ingredient, a binder, and the like to a core particle.

Moreover, for purposes such as improvement in the stability of the active ingredient such as the medicinal ingredient, taste masking, means for controlling the dissolution of the active ingredient, and provision of enteric coating properties, a technique for film coating a granule produced using a core particle has been known.

A film-coated granule has been directly administered as a fine granule, or from the viewpoint of ease of handling, it has been placed into a capsule and then administered in many cases. In recent years, however, from the viewpoint of ease of consumption and reduction in cost, the development of, what is called, a granule-containing tablet, produced by compressing a film-coated granule and excipients, has been progressing. Among others, with the aging of population and changes in the living environment, an orally-disintegrating tablet, which can be easily consumed, while maintaining ease of handling that is characteristic of tablets, and which can be easily consumed at any time anywhere without water, has been under development.

By the way, as core particles used in the production of granules, the following core particles have been known, for example.

Patent Document 1 discloses a film coating method which comprises layering a medicinal ingredient to a sugar core particle and then film coating the thus obtained core particle. Patent Document 2 discloses a method of laminating a drug to microcrystalline cellulose used as a core particle and further film coating the core particle. In addition, Patent Document 3 describes a method for producing a spherical granule containing 20% or more of fine microcrystalline cellulose, which is used as a coated granule. Moreover, Patent Document 4 discloses a pharmaceutically inactive spherical core containing 50% or more of microcrystalline cellulose having a mean degree of polymerization of from 60 to 375, and a film coating method comprising layering a drug to the spherical core. Furthermore, Patent Document 5 discloses: a cellulose pharmaceutical particle obtained by mechanically crushing cellulose to obtain microcrystalline cellulose, preparing a dispersion of the microcrystalline cellulose, converting the dispersion to the form of liquid droplets, and drying the droplets; and a film coating method, which comprises laminating medicinal ingredients to the thus obtained particles. Still further, Patent Document 6 discloses a spherical core containing 0% to 95% by weight of microcrystalline cellulose and 5% to 100% by weight of trehalose.

Patent Document 1: Japanese Patent Laid-Open No. 61-1614
Patent Document 2: Japanese Patent Laid-Open No. 2000-109426
Patent Document 3: Japanese Patent Publication No. 7-2761
Patent Document 4: Japanese Patent No. 2542122
Patent Document 5: International Publication No. WO02/36168
Patent Document 6: Japanese Patent Laid-Open No. 2001-172430

DISCLOSURE OF THE INVENTION

Problems to be Solved by the Invention

However, the sugar core particle disclosed in Patent Document 1 has been problematic in respect of the following (1) to (3).
(1) During the layering of a drug-containing coating layer using an aqueous drug suspension or during film coating using an aqueous coating liquid, sugar used as a main ingredient of such a core particle is dissolved and the surface thereby becomes sticky. Thus, core particles easily become aggregated with one another.
(2) Such core particles have low strength and thus easily become abraded in the process of fluidization. Thus, aggregation of the core particles and adhesion of the core particles to the wall of a coating machine easily take place, resulting in deterioration in yields.
(3) Such a core particle is problematic in that, since the particle is large in size, it causes sandy feeling in the oral cavity when it is applied to a fine granule, an orally-disintegrating tablet, etc.

Moreover, the core particle consisting of microcrystalline cellulose disclosed in Patent Document 2 has been problematic in respect of the following (1) to (3)
(1) Since the core particle has a low tapped bulk density, it adheres to a bug filter on the upper portion of a coating machine when a coating layer and a film coating layer are formed.
(2) Fluidity in a coating machine becomes insufficient.
(3) It is difficult to perform the layering of a drug-containing coating layer or film coating because such core particles easily become abraded and thus granules having a uniform grain size distribution cannot be obtained.

Furthermore, the spherical granule disclosed in Patent Document 3 has been problematic in that the spherical granule has a large particle diameter (150 μm or greater) and thereby causes sandy feeling in the oral cavity when it is applied to a fine granule, a granule-containing tablet, etc., and also in that separation/segregation of granules from excipients takes place when it is processed into such granule-containing tablet.

Still further, the spherical core particle disclosed in Patent Document 4 has been problematic in that the spherical core particle has a large mean particle diameter (100 μm or greater) and thereby causes sandy feeling in the oral cavity when it is applied to a fine granule, a granule-containing tablet, etc., and also in that separation/segregation of granules from excipients takes place when it is processed into such granule-containing tablet.

Still further, the cellulose pharmaceutical core particle described in Patent Document 5 has been problematic in respect of the following (1) and (2).
(1) Since the particle surface has great asperities and the specific surface area is large, the thickness of a film coating layer varies. Thus, it is difficult to control the dissolution of a medicinal ingredient. In order to control the dissolution of a desired medicinal ingredient, it is necessary to thicken the film, and a coating amount must be increased to do so.
(2) Since fluidity is poor when core particles are compressed, the core particles easily accumulate at the bottom of a coating machine. Thus, the fluidity of the core particles becomes poor in a fluidized bed portion for spraying a coating liquid. As a result, application of the coating liquid becomes insufficient, and it thereby becomes difficult to control the dissolution of a medicinal ingredient.

In addition, with regard to the spherical core disclosed in Patent Document 6, it is essential to mix trehalose therewith. Since stikiness is generated because of the high water-solubility of trehalose, it is difficult to prepare a fine core particle of less than 100 µm. Even in a case in which a particle of less than 100 µm can be obtained, it is problematic in that, due to the stikiness of trehalose, aggregation of the core particles easily takes place during drug layering and film coating.

Hence, it has not been possible for the conventional core particles to produce, at a high yield, a small granule comprising a coating layer and a film coating layer each having a uniform thickness.

It is an object of the present invention to provide a fine core particle, which comprises a coating layer and a film coating layer each having a uniform thickness, and which can be used to produce, at a high yield, a small granule causing no sandy feeling in the oral cavity when the fine core particle is applied to a fine granule or an orally-disintegrating tablet.

Means for Solving the Problems

As a result of intensive studies, the present inventors have found that the aforementioned object can be achieved using a core particle, which comprises 50% by mass or more of microcrystalline cellulose and which has a mean particle diameter of less than 100 µm, a relative flow index of 7.0 to 30.0, a specific surface area of less than 0.15 m$^2$/g, and a tapped bulk density of 0.80 g/mL or more. The inventors have also found that such a core particle can be produced by combining the step of granulating particles by stirring and mixing microcrystalline cellulose and a binder liquid with the step of spraying a binder liquid to the particles obtained in the previous step, while allowing the particles to flow by a stream of air and also rotating the particles, thereby completing the present invention.

Specifically, the core particle of the present invention is as follows:
a core particle, which comprises 50% by mass or more of microcrystalline cellulose, and which has
a mean particle diameter of less than 100 µm,
a relative flow index of 7.0 to 30.0,
a specific surface area of less than 0.15 m$^2$/g, and
a tapped bulk density of 0.80 g/mL or more.

Moreover, a process for producing the core particle of the present invention is as follows:
a process for producing a core particle, which comprises the steps of
granulating a particle by stirring and mixing microcrystalline cellulose and a binder liquid; and
spraying a binder liquid to the particle obtained in the previous step, while allowing the particle to flow by a stream of air and also rotating the particle.

Advantage of the Invention

Use of the core particle of the present invention enables the production of a granule, which comprises a coating layer and a film coating layer each having a uniform thickness, easily controls the dissolution of active ingredients, and has a small degree of separation/segregation of the granule from excipients when the core particle is processed into an orally-disintegrating tablet, causing a small degree of sandy feeling in the oral cavity.

BEST MODE FOR CARRYING OUT THE INVENTION

The best mode for carrying out the present invention (hereinafter simply referred to as "the present embodiment") will be described in detail below. The present invention is not limited to the following embodiments, and various changes and modifications may be made within the scope of the gist of the present invention.

The core particle of the present embodiment comprises 50% by mass or more of microcrystalline cellulose and has a mean particle diameter of less than 100 µm, a relative flow index of 7.0 to 30.0, a specific surface area of less than 0.15 m$^2$/g, and a tapped bulk density of 0.80 g/mL or more.

The core particle of the present embodiment comprises 50% by mass or more of microcrystalline cellulose. The term "microcrystalline cellulose" used herein refers to microcrystalline cellulose compatible with standards for the "microcrystalline cellulose" of the Japanese Pharmacopoeia, 15th Edition.

By mixing 50% by mass or more of microcrystalline cellulose into the present core particle, a fine core particle, which has a mean particle diameter of less than 100 µm and which satisfies the physical properties determined in the present application, can be obtained. An appropriate strength is imparted to the core particle, and only a small extent of abrasion is generated during layering and film coating. From the viewpoint of strength and abrasion resistance, the core particle comprises 70% by mass or more of, more preferably 80% by mass or more of, and further preferably 95% by mass or more of microcrystalline cellulose. From the viewpoint of simplification of pharmaceutical preparation, the core particle most preferably comprises 100% by mass of microcrystalline cellulose.

Microcrystalline cellulose used in the present embodiment preferably has a mean degree of polymerization of 60 to 350. Such microcrystalline cellulose can be obtained by hydrolyzing a cellulose material such as a linter, a pulp, or a regenerated fiber, by acid hydrolysis, alkali hydrolysis, steam explosion decomposition, or the combined use thereof. It is also preferable to perform a mechanical treatment before or after such hydrolysis.

If the mean degree of polymerization of microcrystalline cellulose exceeds 350, the core particle has fibrous properties, and it is hardly crushed and the sphericity of the core particle becomes low. Thus, it is not favorable. On the other hand, if the mean degree of polymerization is less than 60, the entanglement of microcrystalline cellulose molecules is reduced, and the hardness of the core particle becomes insufficient. Thus, it is not favorable, either. The mean degree of polymerization of microcrystalline cellulose is preferably 100 to 300, and more preferably 120 to 270.

Examples of ingredients other than microcrystalline cellulose, which may be contained in the core particle of the present embodiment, include: ingredients that can be generally used for pharmaceutical products and food products, such as binders (for example, hypromellose, hydroxypropylcellulose, polyvinyl alcohol, povidone, macrogol, etc.); film coating agents (for example, hypromellose phthalate, hydroxypropylmethylcellulose acetate succinate, carboxymethylethylcellulose, ethyl cellulose, ethyl cellulose aqueous dispersion, aminoalkyl methacrylate copolymer E, methacrylate copolymer L, methacrylate copolymer S, methacrylate copolymer LD, aminoalkyl methacrylate copolymer RS, hydrogenated oil, etc.); surfactants (for example, sucrose fatty acid ester, polyoxyethylene polyoxypropylene glycol, polysorbate, sodium lauryl sulfate, etc.); excipients (for example, corn starch, potato starch, rice starch, powdered sugar, lactose, D-mannitol, trehalose, microcrystalline cellulose-carmellose sodium, etc.); disintegrators (for example, low-substituted hydroxypropylcellulose, carmellose calcium, croscarmellose sodium, partially pregelatinized starch, etc.), inorganic substances (for example, talc, magnesium stearate, light anhydrous silicic acid, synthetic aluminum silicate, titanium oxide, etc.); and other additives.

The core particle of the present embodiment has a mean particle diameter of less than 100 μm. The term "mean particle diameter" used herein refers to a mean value, which is obtained by measuring granular size distribution using a common sieving machine such as a Ro-Tap sieving machine, a shaking type sieving machine, an ultrasonic sieving machine, or an air-dispersion-type sieve analyzer generally known as an air jet sieve, then measuring a cumulative total of 50% by mass of granularity three times, and then calculating a mean value.

From the viewpoint of no aggregation occurring during layering and film coating, the mean particle diameter of the core particle of the present embodiment is preferably 10 μm or more, more preferably 30 μm or more, and further preferably 50 μm or more. From the viewpoint of prevention of sandy feeling felt in the oral cavity when the core particle is applied to a fine granule or an orally-disintegrating tablet, or from the viewpoint of suppression of separation/segregation of granules from excipients when the core particle is applied to a granule-containing tablet, the mean particle diameter of the core particle of the present embodiment is preferably less than 100 μm, and more preferably 90 μm or less. The mean particle diameter of the core particle of the present embodiment is preferably from 10 μm or more to less than 100 μm, more preferably from 30 μm or more to less than 100 μm, further preferably from 50 μm or more to less than 100 μm, and most preferably from 50 μm or more to 90 μm or less.

Moreover, in the present embodiment, the granular size distribution of a core particle is preferably as narrow as possible. The ratio of particles having a particle diameter of 125 μm or more is preferably 10% by mass or less. If the ratio of such particles having a particle diameter of 125 μm or more exceeds 10% by mass, the ratio of large particles increases, and granules prepared using such large particles cause significant sandy feeling in the oral cavity. This is not favorable. Herein, the expression "ratio of particles having a particle diameter of 125 μm or more" used herein refers to a ratio of particles remaining in a sieve with a size of 125 μm or more, when granular size distribution is obtained using a common sieving machine such a Ro-Tap sieving machine, a shaking type sieving machine, an ultrasonic sieving machine, or an air-dispersion-type sieve analyzer generally known as an air jet sieve.

Also, the ratio of particles having a particle diameter smaller than the mean particle diameter is preferably as low as possible. A value of D50/D10 is preferably 2.0 or less, and more preferably 1.6 or less.

The terms "D10" and "D50" used herein refers to granularity of sieve integration 10% and the granularity of sieve integration 50%, respectively, which are obtained when granular size distribution is obtained using the aforementioned common sieving machine. D50 has the same meanings as those of a mean particle diameter. If the D50/D10 value is greater than 2.0, it means that particles with a particle diameter that is a half of or smaller than the mean particle diameter account for 10% or more of all particles. This results in an ununiform thickness of a film during film coating, and thus it is unfavorable.

The granular size distribution of particles having a particle diameter of 32 μm or less is preferably measured using an air-dispersion-type sieve analyzer generally known as an air jet sieve. Specifically, granular size distribution can be obtained by sieving 5 g of a sample for 5 minutes using a sieve of a desired opening size, and then measuring the mass of particles that have passed through such sieve.

The relative flow index of the core particle of the present embodiment is 7.0 to 30.0, preferably 7.0 to 15.0, and more preferably 8.0 to 13.0.

In the present embodiment, the term "relative flow index" used herein refers to an index regarding the fluidity of powders. It is represented as maximum compression stress/uniaxial disintegration stress, which is obtained when the maximum compression stress is 30 kPa.

Relative flow index=maximum compression stress (=30)/uniaxial disintegration stress Herein, the "maximum compression stress" refers to power [kPa] used to compress an aggregate of core particles, and the "uniaxial disintegration stress" refers to shearing stress [kPa] necessary for disintegrating the compressed aggregate of core particles and initiating fluidity. The two types of stresses are represented by the following formulae 1 and 2:

Maximum compression stress [kPa]=$(A-(A\sin^2\theta-\tau^2\cos^2\theta)^{0.5})/\cos^2\theta)\times(1+\sin\theta)-(C/\tan\theta)$    (Formula 1)

wherein $A=\sigma+C/\tan\theta$

Uniaxial disintegration stress [kPa]=$2\times C(1+\sin\theta)/\cos\theta$    (Formula 2)

In the above formulae, C represents cohesion [kPa]; θ represents angle of internal friction; τ represents shearing force [kPa]; and σ represents vertical load [kPa].

The symbol C represents cohesion [kPa], which indicates the binding force between core particles.

The symbol θ represents an angle of internal friction, which indicates force necessary for core particles to move and slide past each other. That is to say, frictional resistance caused by internal friction when a vertically loaded core particle aggregate is sheared in a horizontal direction is proportional to the vertical load. The angle of internal friction is the angle θ obtained when a proportional constant is defined as tan θ in the above case.

The symbol τ represents shearing stress [kPa], and it means force necessary for shearing the vertically loaded core particle aggregate.

The relative flow index is obtained by the following measurement method, for example.

First, C and θ are obtained as follows.

For the measurement, a particulate fluidity measurement apparatus, ShearScan TS-12 (product name; distributed by Nihon Rufuto Co., Ltd.) can be used. A special rotation cell vessel is filled with 30 mL of sample core particles (the particles are leveled off in the vessel), and a head cell is then put down. The vertical load σ is first applied between two parallel rings separated with a slight space, so as to compress the sample core particles. The lower ring is moved towards the upper ring in a state in which the vertical load a is applied. When the state has reached a steady state, the shearing force τ necessary for shearing the sample core particle aggregate is obtained. After the state has reached a steady state, the vertical load is decreased at a certain rate, and a decrease in the shearing force is measured at that time. With regard to the obtained data of the vertical load and shearing force, the vertical load is plotted to the x axis, and the shearing force is plotted to the y axis. This plot is called a yield locus, and the y section of the yield locus represents the cohesion C and the inclination represents the angle of internal friction θ. Using the thus obtained C and θ values, (Formula 1), and (Formula 2), the maximum compression stress and uniaxial disintegration stress under the vertical load σ are obtained.

Herein, for example, 4 standard types of vertical loads (3, 6, 9, and 15 kPa) are applied as such vertical load σ, and under each vertical load σ, the maximum compression stress and uniaxial disintegration stress are calculated by the aforementioned method.

Subsequently, with regard to the maximum compression stress and uniaxial disintegration stress obtained under each vertical load σ, the uniaxial disintegration stress is plotted to the y axis, and the maximum compression stress is plotted to the x axis. In the aforementioned example, 4 points are plotted, and an approximate line is then obtained from such plot. Using this approximate line, the uniaxial disintegration stress when the maximum compression stress is 30 kPa is obtained, and thus a relative flow index is then obtained.

The larger the relative flow index, the smaller the shearing stress necessary for initiation of fluidity, with respect to the maximum compression stress used in compression. Thus, the fluidity of core particles becomes good. In contrast, the smaller the relative flow index, the larger the shearing stress necessary for initiation of fluidity. Thus, in this case, the fluidity of core particles becomes poor.

If the relative flow index is smaller than 7.0, it becomes difficult to form an uniform coating layer around core particles, or to form a film coating layer around granules produced using such core particles.

That is, layering liquid or film coating liquid sprayed and attached to core particles and granules is developed by the movement of particles and the contact of particles with other particles, so that a uniform coating layer or film coating layer can be formed. However, if the relative flow index of core particles is smaller than 7.0, the fluidity of core particles and the fluidity of granules produced using the core particles become deteriorated. As a result, it becomes difficult to form a uniform coating layer or film coating layer. When a coating layer or a film coating layer is not uniform, it becomes difficult to control the dissolution of active ingredients such as medicinal ingredients.

Furthermore, if the relative flow index is smaller than 7.0, the movements of particles and granules become deteriorated, and thus, retention of such particles and granules in a layering apparatus and a coating apparatus easily takes place. As a result, the amount of a layering liquid or film coating liquid adhered varies, and a coating layer or film coating layer becomes inconveniently ununiform.

On the other hand, if the relative flow index is greater than 30.0, core particles easily roll because the fluidity of the core particles is too high, and ease of handling thereby becomes deteriorated. In addition, when a granule-containing tablet is prepared by mixing excipients with a granule formed by coating a core particle with a relative flow index of greater than 30.0 with a coating layer, the fluidity of the granule is too high with respect to the powder of the excipients, and it causes separation/segregation of the granule from the excipients. When the mean particle diameter of core particles is more than 100 μm, the core particles are large in size, and the surface area thereof is thereby reduced. Thus, the contact points of the core particles with the excipients are reduced, and the entanglement of the core particles with the excipients is also reduced. As a result, in the case of a relative flow index of smaller than 30.0 as well, separation/segregation of granules from excipients easily takes place.

The specific surface area of the core particles of the present embodiment measured by the BET method is less than 0.15 $m^2/g$, and preferably 0.02 to 0.145 $m^2/g$.

If the specific surface area of the core particles is 0.15 $m^2/g$ or more, many microasperities are generated on the surface of the core particle. Thus, when a coating layer is formed on the core particle by a layering method to produce a granule, the layered amounts of individual particles are likely to vary. Moreover, if there are many microasperities on the surface of the core particle, when a film coating layer is formed on the granule produced using the core particle according to a film coating method, so as to produce a film-coated granule, the thickness of such film coating layer becomes ununiform, so that it becomes difficult to control the dissolution of active ingredients contained in the coating layer, such as medicinal ingredients, and so that dissolution times are likely to vary. In order to control the dissolution of such active ingredients without variation, the thickness of a film coating layer may be increased. In order to increase the thickness of such film coating layer, the film coating amount must be increased. Thus, this is unfavorable because it requires operating cost and raw material cost.

In the case of the core particle of the present embodiment, the mean particle diameter is less than 100 μm, and thus particles are small in size. Accordingly, in particular, in order to form a uniform film coating layer, the number of microasperities on the surface of the particle is preferably small.

If the specific surface area of core particles is 0.15 $m^2/g$ or more, when an aqueous coating liquid is sprayed to a granule produced using the core particle at a high rate, adhesion or aggregation hardly takes place. On the other hand, as mentioned above, in order to control the dissolution of active ingredients from a film coating layer, a large amount of coating liquid must be applied to a granule produced using a core particle having a large specific surface area. Accordingly, with all things considered, productivity is not significantly increased.

The tapped bulk density of the core particle of the present embodiment is 0.80 g/mL or more, and preferably 0.80 to 1.20 g/mL.

The term "tapped bulk density" used herein refers to a value (g/mL) obtained by roughly filling a 100-mL glass measuring cylinder with 30 g of core particles, then tapping it with a hand until a decrease in the volume of the particle layer has stopped, then reading the volume (mL) of the particle layer, and then dividing the obtained value by 30.

If the tapped bulk density is less than 0.80 g/mL, each particle becomes light, and the number of particles per unit mass increases. Thereby, the surface area of particles per unit mass also increases. As a result, in order to obtain a film coating layer having a thickness necessary for the control of the dissolution of active ingredients contained in a coating layer, the film coating amount must be increased.

In the case of the core particle of the present embodiment, since the mean particle diameter is small (less than 100 μm), a slight difference in the tapped bulk density has a great effect on the number of particles per unit mass. Thus, a tapped bulk density that is large is particularly important.

It is preferable that the core particle of the present embodiment have a minor axis/major axis ratio of 0.7 or greater and a surface smoothing shape factor of 0.925 or greater. More preferably, the minor axis/major axis ratio is 0.7 or greater, and a surface smoothing shape factor is 0.930 or greater.

Herein, the term "minor axis/major axis ratio" used herein refers to a ratio of the mean minor axis of particles to the mean major axis thereof (mean minor axis/mean major axis). The terms "minor axis" and "major axis" used herein refer to a short side and a long side of a circumscribed square in which an area circumscribing on the boundary pixel of a particle becomes minimum, respectively.

Moreover, the surface smoothing shape factor is an index that represents a roundness or ovalness of a particle, which is represented by the following formula.

Surface smoothing shape factor=[π×(major axis of particle+minor axis of particle)]/[2×boundary length of particle]

When a particle has a completely round shape, its surface smoothing shape factor becomes 1. When a particle has a completely oval shape, its surface smoothing shape factor becomes almost 1. When a particle does not have a smooth round or oval shape, but has an irregular shape, the boundary length of the particle increases. Thus, the surface smoothing shape factor thereby becomes smaller than 1.

If the minor axis/major axis ratio is less than 0.7, the core particle has an irregular shape. Thus, in a case in which a film coating layer is formed on a granule produced using the aforementioned core particle, it becomes difficult to control the dissolution of active ingredients from a coating layer. In addition, the relative flow index easily becomes less than 7.0, and the fluidity of core particles easily becomes poor. Thus, this is not favorable.

Further, when the surface smoothing shape factor is less than 0.925, the core particle may not have a smooth round or oval shape, but it may have an irregular concavo-convex shape in many cases. Thus, the thickness of a film coating layer formed on a granule according to a coating method becomes uneven. As a result, it becomes difficult to control dissolution of active ingredients from a coating layer, and dissolution times are like to vary. Still further, due to such irregular concavo-convex shape of a core particle, the relative flow index becomes smaller than 7.0, and the fluidity of core particles thereby becomes poor.

In the present embodiment, the amount of water vapor adsorbed on a core particle is preferably 1.50% or more, and more preferably 2.00% to 5.00%.

The term "amount of water vapor adsorbed" used herein refers to an amount of water vapor adsorbed on a core particle at a relative humidity (RH) of 30%, and it is represented by the following formula.

Amount of water vapor adsorbed [%]={(core particle mass at relative humidity (RH) of 30%–core particle mass at relative humidity (RH) of 0%)/core particle mass at relative humidity (RH) of 0%}× 100

If the amount of water vapor adsorbed is less than 1.50%, the water-absorbing properties of the core particle become insufficient. Thus, when an aqueous layer solution or an aqueous coating liquid is used for layering or film coating, aggregation of core particles or granules and adhesion of them to the wall of a machine frequently take place. Thus, it is not favorable.

A core particle having the aforementioned physical properties can be obtained by a method for producing core particles, which comprises the steps of granulating particles by stirring and mixing microcrystalline cellulose and a binder liquid; and spraying a binder liquid to the particles obtained in the previous step, while allowing the particles to flow by a stream of air and also rotating the particles.

First, the step of granulating particles by stirring and mixing microcrystalline cellulose and a binder liquid will be described.

In the present embodiment, the binder liquid is not particularly limited, as long as it is a liquid capable of binding microcrystalline cellulose. From the viewpoint of ease of handling, water such as distilled water can be preferably used. Instead of such distilled water, an aqueous solution of hydroxypropylcellulose, starch paste, povidone (polyvinylpyrrolidone), etc. may also be used as a binder liquid.

A mixing and stirring granulator is preferably used to stir and mix microcrystalline cellulose and a binder liquid. In addition, when microcrystalline cellulose and a binder liquid are stirred and mixed, ingredients other than the microcrystalline cellulose acting as a constitutional ingredient of the core particles and the binder liquid, such as an excipient and a disintegrator, may be added.

Specifically, in this step, it is preferable that distilled water be added to and mixed with powders containing 50% by mass or more of microcrystalline cellulose, while blending the powders using a mixing and stirring granulator.

Next, the step of spraying a binder liquid to the particles obtained in the previous step, while fluidizing the particles by a stream of air and also rotating the particles, will be described.

As a binder liquid that is sprayed to the particles in this step, any type of binder liquid may be used, as long as it is able to bind microcrystalline cellulose. Thus, it may be identical to or different from the binder liquid used in the granulation step. From the viewpoint of ease of handling, water such as distilled water can preferably be used.

Moreover, for the fluidizing and rotation of the particles, a rotating and fluidized bed-type coating apparatus is preferably used.

Specifically, in this step, it is preferable that the particles obtained in the granulation step be transferred into a rotating and fluidized bed-type coating apparatus, the particles be fluidized by supplying the air from the bottom portion, and distilled water be sprayed to the particles, while rotating them by the rotation of a rolling board at the bottom, namely, while rolling them.

The particles are weighed and spheronized by this step, are then dried, and are then sieved if necessary, so as to produce core particles of less than approximately 100 μm, which satisfy the physical properties specified in the present specification.

In the case of applying a method for producing core particles having a mean particle diameter of less than 100 μm from fine microcrystalline cellulose powders only using a rotating and fluidized bed-type coating apparatus, namely, in the case of applying the method described in cited document 3, the amount of water supplied needs to be decreased, as compared to that in the method described in cited document 3. This is because the shearing force applied to particles in a granulation method involving the rotation of a rolling board is smaller than that in a granulation method involving stirring and mixing, and because particles are gathered if the amount of water supplied is increased and thus the mean particle diameter easily becomes 100 μm or more. However, if the amount of water supplied is decreased to produce core particles of less than 100 μm, a heavy core particle with a tapped bulk density of 0.80 g/mL or more, or a smooth core particle with a surface smoothing shape factor of 0.925 or more cannot be obtained. This is because, since the force for sufficiently compressing and spheronizing particles cannot be obtained only with the use of a rotating and fluidized bed-type coating apparatus, sufficiently heavy particles can hardly be obtained from fine microcrystalline cellulose powders. In addition, a decrease in the amount of water supplied makes it further difficult to sufficiently compress and spheronize core particles. Accordingly, only using a rotating and fluidized bed-type coating apparatus, it is impossible to produce core particles, which has a mean particle diameter of 100 µm and satisfies the aforementioned tapped bulk density and surface smoothing shape factor.

Moreover, as described in cited document 4, in a case in which particles are mixed using a mixing and stirring granulator, and thereafter, core particles having a mean particle diameter of less than 100 µm are produced using a rotating-type coating apparatus such as Marumerizer, the amount of water supplied needs to be decreased, as compared to that in the method described in cited document 4. In the case of such rotating-type coating apparatus, particles are not fluidized by supplying the air, and the particle surface easily gets wet. Thus, if the amount of water added is increased, particles are aggregated, and as a result, it becomes impossible to produce small core particles having a mean particle diameter of less than 100 µm. On the other hand, if particles are mixed using a mixing and stirring granulator and the amount of water supplied is then decreased using a rotating-type coating apparatus to produce core particles having a mean particle diameter of less than 100 µm, the particles cannot be sufficiently weighted and spheronized, and as a result, a heavy core particle with a tapped bulk density of 0.80 g/mL or more, or a smooth core particle with a surface smoothing shape factor of 0.925 or more cannot be obtained. In order to suppress aggregation of particles, it is necessary to reduce the amount of water supplied to minimum. Accordingly, by the method of mixing particles using a mixing and stirring granulator and then using a rotating-type coating apparatus such as Marumerizer, core particles having a particle diameter of less than 100 µm and satisfying the aforementioned tapped bulk density and surface smoothing shape factor cannot be obtained.

Differing from the aforementioned techniques, cited document 5 discloses a method for producing core particles, which comprises mechanically crushing core particles having a mean particle diameter of less than 100 µm and a high tapped bulk density, preparing a dispersion comprising the obtained microcrystalline cellulose, and then converting the dispersion to the form of liquid droplets, followed by drying the droplets. However, in this method, core particles are produced by aggregating the crushed particles of 15 µm or less by spray-drying. Thus, there are many asperities on the surface of such particle. As a result, a core particle having a high tapped bulk density, which also has a relative flow index of 7.0 to 30.0 and a specific surface area of less than 15.0 m$^2$/g, cannot be obtained.

Therefore, by the method of mechanically crushing particles, preparing a dispersion containing the obtained microcrystalline cellulose, and converting the dispersion to the form of liquid droplets, followed by drying the droplets, core particles each having a particle diameter of less than 100 µm and, at the same time, satisfying physical properties such as relative flow index and specific surface area cannot be obtained.

As described above, a core particle, which has a mean particle diameter of less than 100 µm, and which is also heavy and highly spherical and has a smooth surface, has not been produced so far.

However, as in the present embodiment, by stirring and mixing particles using a mixing and stirring granulator or the like previously to form compressed and spheronized particles and then spraying a binder liquid such as distilled water to the particles while fluidizing and rotating the particles, it became possible for the first time to produce core particles, which have a mean particle diameter of less than 100 µm, and which is also heavy and highly spherical and has a smooth surface.

Since a strong shearing force is added by stirring and mixing microcrystalline cellulose and a binder liquid, particles of less than 100 µm can be first granulated. Thereafter, particles are continuously rotated, while wetting and drying them repeatedly, so as to progress the compression and spheronization of the particles. At the time, around the bottom of the rotating and fluidized bed-type coating apparatus, the binder liquid is sprayed to the particles, and at the same time, the shearing force of a rolling board is added. As a result, the compression and spheronization of the particles further progress. Thereafter, the particles are fluidized by supplying the air. At the time, water attached to the surface of the particle is removed by drying. Thus, even in a case in which the particles are gathered at the bottom, they can be separated again soon. Hence, in the rotating and fluidized bed-type coating apparatus, it becomes possible to supply a binder liquid in an amount sufficient for the compression and spheronization of the particles.

Thus, the production method of the present embodiment made it possible to promote the compression and spheronization of particles without aggregation thereof. Accordingly, it became possible to produce fine core particles, which have a mean particle diameter of less than 100 µm, and which are heavy and have smooth surface.

The core particle of the present embodiment is suitable to produce a granule comprising the core particle and a coating layer that coats the core particle.

In the present embodiment, a coating layer may comprise ingredients with desired properties as active ingredients. Examples of such active ingredient include an aroma chemical, a flavor, and a medicinal ingredient.

The core particle of the present embodiment has a small particle diameter and is able to form a coating layer, which is uniform in thickness and easily controls the dissolution of active ingredients. Thus, the present core particle is particularly suitable to produce a granule coated with a medicinal ingredient-containing coating layer.

Examples of the medicinal ingredient that can be used in the present embodiment include medicinal ingredients used in the treatment, prevention, and diagnosis of human and animal diseases. Specific examples of such medicinal ingredient include: antiepileptic agents (acetylpheneturide, primidone, etc.); antipyretic analgesic antiphlogistic agents (acetaminophen, phenylacetylglycinemethylamide, diclofenac sodium, oxyphenbutazone, sulpyrine, ibuprofen, ethenzamide, ketoprofen, tinoridine hydrochloride, benzydamine hydrochloride, tiaramide hydrochloride, piroxicam, loxoprofen sodium, etc.); antivertiginous agents (dimenhydrinate, difenidol hydrochloride, etc.); psychoneurotic agents (chlorpromazine hydrochloride, levomepromazine maleate, perazine maleate, perphenazine, diazepam, oxazepam, etc.); skeletal muscle relaxants (chlorzoxazone, chlorphenesin carbamate, chlormezanone, eperisone hydrochloride, etc.); autonomic agents (bethanechol chloride, neostigmine bromide, pyridostigmine bromide, etc.); antispasmodic agents (butropium bromide, scopolamine butylbromide, propantheline bromide, papaverine hydrochloride, etc.); antiparkinson agents (trihexyphenidyl hydrochloride, etc.); antihistaminic agents (diphenhydramine hydrochloride, dl-chlorpheniramine maleate, d-chlorpheniramine maleate, promethazine, mequitazine, etc.); cardiac stimulants (aminophylline, caffeine, dl-isoproterenol hydrochloride, etilefrine hydrochloride, etc.); antiarrhythmic agents (disopyramide, etc.);

diuretics (potassium chloride, hydrochlorothiazide, acetazolamide, etc.); hypotensive agents (hexamethonium bromide, hydralazine hydrochloride, propranolol hydrochloride, captopril, methyldopa, etc.); vasodilators (etafenone hydrochloride, carbocromen hydrochloride, pentaerythritol tetranitrate, dipyridamole, nicametate citrate, etc.); drugs for arteriosclerosis (lecithin, etc.); drugs for circulatory organs (nicardipine hydrochloride, meclofenoxate hydrochloride, pyridinol carbamate, calcium hopantenate, pentoxifylline, etc.); respiratory stimulants (dimefline hydrochloride, etc.); antitussive expectorant agents (dextromethorphan hydrobromide, noscapine, L-methylcysteine hydrochloride, theophylline, ephedrine hydrochloride, etc.); cholagogues (dehydrocholic acid, etc.); drugs for digestive organs (metoclopramide, domperidone, etc.); vitamins (riboflavin, fursultiamine, octotiamine, pyridoxine hydrochloride, nicotinic acid, ascorbic acid, etc.); antibiotics (erythromycin, Kitasamycin, Josamycin, tetracycline, etc.); and chemotherapeutic agents (isoniazid, ethionamide, nitrofurantoin, enoxacin, ofloxacin, norfloxacin, etc.).

In the present embodiment, a core particle may be coated with two or more types of medicinal ingredients, simultaneously or successively.

The coating amount of the medicinal ingredient may be determined, as appropriate, depending on the dosage of the medicinal ingredient. In the case of the medicinal ingredient that performs its drug effect even in a trace amount, approximately 0.01 part by mass of the medicinal ingredient may preferably be used based on 100 parts by mass of core particles. In a case in which a large amount of medicinal ingredient is required for the performance of its drug effect, approximately 200 parts by mass of the medicinal ingredient may preferably used based on 100 parts by mass of core particles.

Furthermore, from the viewpoint of prevention of aggregation occurring during film coating, the mean particle diameter of granules produced using the core particles of the present embodiment is preferably 10 μm or more, more preferably 30 μm or more, and further preferably 50 μm. From the viewpoint of prevention of sandy feeling in the oral cavity when the granules of the present embodiment are applied to a fine granule or an orally-disintegrating tablet, or from the viewpoint of suppression of separation/segregation of granules from excipients when the granules of the present embodiment are applied to a grain-containing tablet, the mean particle diameter of the granules of the present embodiment is preferably less than 100 μm, and more preferably 90 μm or less. Thus, the mean particle diameter of the granules of the present embodiment is preferably from 10 μm or more to less than 100 μm, more preferably from 30 μm or more to less than 100 μm, further preferably from 50 μm or more to less than 100 μm, and most preferably from 50 μm or more to 90 μm or less. In addition, from the viewpoint of the achievement of a film having a uniform thickness during film coating, the granular size distribution of granules is preferably sharp. When the mean particle diameter is from 50 μm or more to less than 100 μm, it is most preferable that the ratio of particles having a particle diameter of 125 μm or more be 10% by mass or less and the ratio of particles having a particle diameter of less than 32 μm be 10% by mass or less.

Examples of a method for producing granules by coating the core particles of the present embodiment with a coating layer containing an active ingredient are as follows:

(1) a method, which comprises spraying a solution prepared by dissolving or suspending an active ingredient in a binder liquid to core particles, while fluidizing the core particles using a fluidized-bed granulation coating apparatus (or a rotating and fluidized bed-type coating apparatus, a Wurster column-equipped fluidized-bed granulation coating apparatus, a modified Wurster column-equipped fluidized-bed granulation coating apparatus, etc.);

(2) a method, which comprises continuously spraying a binder liquid to core particles while rotating the core particles in a centrifugal fluidized bed-type coating apparatus, and at the same time, dispersing active ingredient powders (an excipient, as necessary);

(3) a method, which comprises adding to core particles an active ingredient and a binder liquid in amounts absorbable by the core particles, while rotating them using a high-speed stirring granulator; and (4) a method of immersing core particles in a solution containing an active ingredient and a binder liquid. In all above methods, an operation of drying core particles and then removing the gathered granules, and the like, may be carried out, as necessary.

When a core particle is coated with a coating layer, for an improvement in workability, or for prevention of the removal of constitutional ingredients from the coating layer in the subsequent process, or for the control or stabilization of the dissolution rate of the active ingredients from the coating layer, the following additives may also be used to form the coating layer: binders (for example, hypromellose, hydroxypropylcellulose, polyvinyl alcohol, povidone, macrogol, etc.); film coating agents (for example, hypromellose phthalate, hydroxypropylmethylcellulose acetate succinate, carboxymethylethylcellulose, ethyl cellulose, ethyl cellulose aqueous dispersion, aminoalkyl methacrylate copolymer E, methacrylate copolymer L, methacrylate copolymer S, methacrylate copolymer LD, aminoalkyl methacrylate copolymer RS, hydrogenated oil, etc.); surfactants (for example, sucrose fatty acid ester, polyoxyethylene polyoxypropylene glycol, polysorbate, sodium lauryl sulfate, etc.); excipients (for example, corn starch, rice starch, powdered sugar, lactose, microcrystalline cellulose, powder cellulose, microcrystalline cellulose-carmellose sodium, etc.); disintegrators (for example, low-substituted hydroxypropylcellulose, carmellose calcium, croscarmellose sodium, partially pregelatinized starch, etc.), inorganic substances (for example, talc, magnesium stearate, light anhydrous silicic acid, synthetic aluminum silicate, titanium oxide, etc.); and other additives.

A medium used to form a coating layer is not particularly specified. For example, water and organic solvents usable in the field of food products and pharmaceutical products, such as ethanol, may be used. A solution prepared by suspending or dissolving an active ingredient, a binder, and the like in such solvent may be used to form a coating layer.

It is preferable that a film coating layer be established on the granule produced from the core particle of the present embodiment, so as to produce a film-coated granule. Film coating is carried out on a granule prepared by coating a core particle with a medicinal ingredient, for example, for purposes such as the improvement of ease of consumption, the improvement of appearance, exclusion of moisture, exclusion of oxygen, the control of the dissolution rate of a drug (for example, sustained-release properties, enteric properties, etc.), and the masking of the bitterness or odor of a drug.

As a film coating agent used in such film coating, a known film coating agent can be used. Examples of such a film coating agent include: water-soluble film coating agents such as aminoalkyl methacrylate copolymer E, hydroxypropylcellulose, or hypromellose; sustained-release film coating agents such as ethyl cellulose, an aqueous dispersion of ethyl cellulose, methacrylate copolymer S, aminoalkyl methacrylate copolymer RS, or ethyl acrylate methyl methacrylate copolymer-emulsion; and enteric film coating agents such as hypromellose phthalate, hydroxypropylmethylcellulose acetate succinate, carboxymethylethylcellulose, methacrylate copolymer L, methacrylate copolymer LD, or methacrylate copolymer S. These coating agents may be used singly or in combination of two or more types. Moreover, it may also be possible that the granule is film-coated with a single coating agent or two or more types of coating agents, and that the thus film-coated granule is then further film-coated with another coating agent containing different ingredients. Furthermore, a water-soluble substance, a plasticizer, a stabilizer, a coloring agent, and the like may also be added thereto to control the dissolution rate of medicinal ingredients, as necessary.

The amount of a film coating agent differs depending on purpose. A film coating layer is used at a mass ratio of preferably 1 to 100 parts by mass, and more preferably 3 to 50 parts by mass, with respect to 100 parts by mass of granules. If more than 100 parts by mass of the film coating layer is used, the size of the film-coated granule becomes large, and it thereby causes sandy feeling in the oral cavity. Thus, this is not favorable. On the other hand, if less than 1 part by mass of the film coating layer is used, not the entire surface of the granule is coated with the film coating layer, and thereby purposes such as the control of dissolution and the masking of bitterness cannot be achieved. Thus, this is not favorable, either.

In the present embodiment, the ratio of particles having a particle diameter of 125 μm or more is preferably 10% by mass or less in the film-coated granules. If the ratio of such particles having a particle diameter of 125 μm or more exceeds 10% by mass, they cause sandy feeling in the oral cavity when they are applied to a fine granule or an orally-disintegrating tablet. Thus, this is unfavorable. Furthermore, when the aforementioned granules are applied to a granule-containing tablet, separation/segregation of granules from excipients easily takes place. Thus, this is unfavorable.

As a method of coating a granule according to a film coating method, a known method can be used. For example, coating can be carried out using a fluidized-bed granulation coating apparatus, a Wurster column-equipped fluidized-bed granulation coating apparatus, a modified Wurster column-equipped fluidized-bed granulation coating apparatus, a centrifugal fluidized bed-type granulation coating apparatus, a rotating and fluidized bed-type granulation coating apparatus, etc.

In the present embodiment, when a granule or a film-coated granule contains a medicinal ingredient, it may be directly administered, or it may be mixed with another agent and may be then administered. It is preferable that such granules or film-coated granules be filled in a capsule to prepare a capsule agent, or that they be mixed with another suitable excipient, and the mixture be then processed into a tablet, thereby preparing a granule-containing tablet. Among such granule-containing tablets, an orally-disintegrating tablet that can be administered without water is a preferred embodiment.

Next, an orally-disintegrating tablet will be described below.

In the present embodiment, 100 parts by mass of orally-disintegrating tablet comprises granules or film-coated granules at a mass ratio of preferably 1 to 90 parts by mass, more preferably 3 to 70 parts by mass, and further preferably 5 to 50 parts by mass. If the granules or the film-coated granules are contained at a mass ratio of less than 1 part by mass, the amount of a medicinal ingredient is small, and its drug effect is not expressed. Thus, this is not favorable. On the other hand, if the granules or the film-coated granules are contained at a mass ratio of more than 90 parts by mass, the orally-disintegrating tablet becomes problematic in that it cannot have sufficient hardness and in that the tablet does not disintegrate in the oral cavity, etc. Thus, this is not favorable, either.

In the present embodiment, the orally-disintegrating tablet preferably comprises cellulose. Such cellulose is mixed at a mass ratio of preferably 1 to 30 parts by mass, and more preferably 2 to 20 parts by mass, with respect to 100 parts by mass of orally-disintegrating tablet. If such cellulose is contained at a mass ratio of less than 1 part by mass, the hardness of the orally-disintegrating tablet unfavorably becomes insufficient. In contrast, if such cellulose is contained at a mass ratio of more than 30 parts by mass, the prepared orally-disintegrating tablet unfavorably causes mealiness in the oral cavity.

Such cellulose includes microcrystalline cellulose, powder cellulose, low-substituted hydroxypropylcellulose, and the like. These celluloses may be used singly or in combination of two or more types. Of these, it is preferable to use microcrystalline cellulose in terms of the balance between the compactibility and disintegrating properties of the orally-disintegrating tablet. Specific examples of microcrystalline cellulose include Ceolus KG-802, KG-1000, PH-101, PH-102, PH-301, PH-302, PH-200, and PH-F20JP (all manufactured by Asahi Kasei Chemicals Corporation).

In the present embodiment, the orally-disintegrating tablet may comprise sugars such as lactose, sucrose or trehalose, or sugar alcohols such as D-mannitol, erythritol, xylitol, maltitol or sorbitol. Of these, lactose, trehalose, and D-mannitol are preferable. These sugars or sugar alcohols may be used singly or in combination of two or more types. Such sugar or sugar alcohol is mixed at a mass ratio of preferably 5 to 90 parts by mass, and more preferably 10 to 80 parts by mass, with respect to 100 parts by mass of the tablet.

Moreover, in the present embodiment, the orally-disintegrating tablet may comprise a disintegrator. Such disintegrator includes croscarmellose sodium, crospovidone, carmellose calcium, carboxymethyl starch sodium, partially pregelatinized starch, and the like. Such disintegrator is mixed at a mass ratio of preferably 0.1 to 15 parts by mass, and more preferably 0.5 to 10 parts by mass, with respect to 100 parts by mass of the tablet.

Furthermore, in the present embodiment, the orally-disintegrating tablet may also comprise, in appropriate amounts, starches such as corn starch, potato starch, rice starch, or pregelatinized starch; inorganic excipients such as anhydrous calcium phosphate; various types of other additives used in production of common pharmaceutical agents, as well as the aforementioned celluloses, sugars, or sugar alcohols. Examples of such additive include an acidulant, a foaming agent, an artificial sweetener, an aroma chemical, a lubricant, a fluidizer, a coloring agent, a stabilizer, a pH adjuster, and a surfactant.

Examples of an acidulant include citric acid, tartaric acid, malic acid, and ascorbic acid. Examples of a foaming agent include sodium bicarbonate and sodium carbonate. Examples of a sweetener include saccharin sodium, dipotassium glycyrrhizinate, aspartame, stevia, and thaumatin. Examples of an aroma chemical include lemon oil, orange oil, and menthol. Examples of a lubricant include magnesium stearate, sucrose fatty acid ester, polyethylene glycol, talc, stearic acid, and sodium stearyl fumarate. Examples of a fluidizer include light anhydrous silicic acid, magnesium aluminometasilicate, and calcium silicate. Examples of a coloring agent include food colorants such as food yellow No. 5, food red No. 2, or food blue No. 2, food lake pigments, and iron sesquioxide. Examples of a stabilizer include sodium edentate, tocopherol, and cyclodextrin. Examples of a pH adjuster include citrate, phosphate, carbonate, tartarate, fumarate, acetate, and amino-acid salts. Examples of a surfactant include sodium lauryl sulfate, polysorbate 80, hydrogenated oil, polyoxyethylene (160), and polyoxypropylene (30) glycol.

A specific method for producing orally-disintegrating tablets is a method comprises mixing film-coated granules with additives including celluloses, sugars, sugar alcohols, etc., using an appropriate mixer, so as to prepare powders to be used in tableting, and then directly making the tablet.

In addition, as a method of preparing such powders to be used in tableting, there may be applied, either a method comprising previously blending additives including celluloses, sugars, sugar alcohols, etc., and then adding film-coated granules thereto, or a method comprising previously mixing film-coated granules with one or two or more types of additives, then further adding other additives to the mixture, and then mixing them. Moreover, additives including celluloses, sugars, sugar alcohols, etc. may be subjected to a wet granulation method, using, as necessary, water in which a binder has been dispersed or dissolved, so as to prepare granules used for tablets, and thereafter, the granules may be mixed with the film-coated granules to prepare powders to be used in tableting.

Among these methods, the direct tableting method, which comprises mixing the film-coated granules with additives including celluloses, sugars, sugar alcohols, etc., and then making a tablet from the mixture, includes simple steps, and it is preferable in terms of costs. The film-coated granules that are preferable in the present embodiment comprise less than 10% by mass of particles having a particle diameter of more than 125 µm. Since such film-coated granules comprise small particles, they are advantageous in that separation/segregation of granules from excipients hardly takes place, when powders to be used in tableting are prepared to obtain orally-disintegrating tablets, or when such powders to be used in tableting are filled in a hopper and supplied to make tablets.

An orally-disintegrating tablet can be produced by making tablets from the aforementioned powders to be used in tableting, using a known tableting machine such as a rotary tableting machine or a single shot tableting machine. A pressure applied during tableting is preferably as low as possible. It is preferably 20 kN or less, more preferably 10 kN or less, and further preferably 5 kN or less. When a high pressure is applied during tableting, the films of film-coated granules contained in an orally-disintegrating tablet are damaged, and the dissolution of medicinal ingredients unfavorably cannot be controlled. Such pressure applied during tableting is determined, as appropriate, depending on the moldability of an excipient, the hardness of a tablet to be produced, and the like.

The shape of a tableting machine consisting of a mortar and a punch used in tableting is not particularly limited. A round, oval, triangular, quadrangular, pentangular, hexangular, star-shaped tableting machine may be used, for example. From the viewpoint of ease of handling when used, a round tableting machine is particularly preferable. In addition, in the case of a round tableting machine, the diameters of the mortar and punch thereof are not particularly limited, as long as they are sufficient for production of ordinary pharmaceutical tablets. Such diameter is preferably 6 to 20 mm, and more preferably 6 to 10 mm. Moreover, the shape of the tableting surface of the punch is not particularly limited, either, as long as it is a shape suitable for production of ordinary pharmaceutical tablets. A flat punch, an R punch, a two-stage R punch, a scored punch, or the like can be used. Furthermore, an imprinting punch may also be used. The material of such punch is not particularly limited, as long as it is a commonly used material. The tableting surface of the punch may be plated with metal such as chromium, or may be polished with an abrasive. Further, the mass of a tablet made using such tableting machine may be determined within the range in which it is used as a common tablet.

The hardness of an orally-disintegrating tablet is preferably 40 N or more. The disintegration time of the tablet in the oral cavity is preferably within 60 seconds. Herein, tablet hardness is defined as a value obtained by using a Schleuniger tablet hardness tester (manufactured by Freund Corporation), applying a load to a tablet in the direction of the diameter thereof 1 day after production of the tablet so as to disintegrate the tablet, then measuring the load necessary for such disintegration, and then obtaining a mean value of the thus measured 10 loads. The oral disintegration time is defined as a time required until a tablet placed in the oral cavity has completely disintegrated therein and the shape of the tablet has completely disappeared.

If the tablet hardness is less than 40 N, when the tablet is filled in a wrapping machine or a bottle, or during transportation, it is easily broken or defaced. Also, when the tablet is taken out of a wrapping paper or a bottle for administration, it is easily broken. Thus, this is not favorable. Moreover, if the oral disintegration time exceeds 60 seconds, since the tablet hardly disintegrates in the oral cavity, it causes an unpleasant feeling such as sandy feeling in the oral cavity. Thus, this is not favorable, either.

In the case of an orally-disintegrating tablet produced using granules obtained from the core particles of the present embodiment, since each film-coated granule has a small particle diameter, the orally-disintegrating tablet is advantageous in that it causes only a small degree of sandy feeling in the oral cavity when it has disintegrated therein. Furthermore, since the dissolution of medicinal ingredients can be easily controlled, the orally-disintegrating tablet is also advantageous in that bitterness hardly comes out due to the dissolution of such medicinal ingredients when the film-coated granules have disintegrated and have been placed on the tongue.

EXAMPLES

Hereinafter, the present invention will be described in detail by the following Examples and Comparative Examples. However, these Examples are not intended to limit the scope of the present invention.

First, measurement methods of the physical properties of a core particle will be summarized below.

Degree of Polymerization of Microcrystalline Cellulose

Identification test (3) of microcrystalline cellulose of the Japanese Pharmacopoeia, 15th Edition, was used.

Mean Particle Diameter [µm] of Core Particles and Granules 30 g of a sample was sieved for 15 minutes, using a JIS standard sieve (Z8801-1987) (sieve openings: 150, 125, 106, 75, 63, 45, and 38 µm), employing a Ro-Tap sieve shaker (Sieve Shaker Type A; manufactured by Hirako Seisakusho Co., Ltd.), so as to measure granular size distribution. The granularity at a cumulative total of 50% by mass was defined as a mean particle diameter. The measurement was repeatedly carried out three times, and a mean value was then obtained.

Ratio of Particles of 125 µm or More [Mass %]

30 g of a sample was sieved for 15 minutes, using a JIS standard sieve (Z8801-1987), employing a Ro-Tap sieve shaker (Sieve Shaker Type A; manufactured by Hirako Seisakusho Co., Ltd.), so as to obtain the aforementioned ratio, based on the mass of particles of 125 µm or more.

Ratio of Particles of 32 μm or Less [Mass %]

5 g of a sample was sieved using a sieve with an opening of 32 μm, employing Air Jet Sieve (manufactured by ALPINE), and the aforementioned ratio was obtained by measuring the mass of particles that had passed through the 32-μm sieve.

The measurement was repeatedly carried out three times, and a mean value was then obtained.

Tapped Bulk Density [g/mL] of Core Particles

A 100-mL glass measuring cylinder was roughly filled with 30 g of core particles, and the measuring cylinder was then tapped with a hand on a low-impact board such as a table placed on a rubber board. Tapping was carried out by vertically dropping the measuring cylinder from a height of several centimeters onto the board. Such tapping was carried out until compression of the particle layer was terminated. After completing of the tapping, the volume (mL) of the particle layer was read. A value obtained by dividing the read value by 30 was defined as a tapped bulk density.

The measurement was repeatedly carried out three times, and a mean value was then obtained.

Minor Axis/Major Axis Ratio of Core Particles

An image taken using a digital microscope (VH-7000 type, VH-501 lens used; manufactured by Keyence Corporation) was preserved at 1360×1024 pixels in a TIFF file form. Using image processing analysis software (Image HyperII; Digimo Co., Ltd.), the minor axis/major axis of each of 100 particles was measured, and a mean value was then obtained.

It is to be noted that the major axis/minor axis ratio becomes 1 when the shape of the particle is completely round, and that as the particle has an irregular shape, the above ratio becomes smaller than 1.

Surface Smoothing Shape Factor of Core Particles

An image taken using a digital microscope was preserved at 1360×1024 pixels in a TIFF file form. Using image processing analysis software, 100 particles were measured in terms of major axis, minor axis, and circumference. Using the obtained values, a surface smoothing shape factor was obtained according to the following formula, and a mean value was then obtained.

$$\text{Surface smoothing shape factor} = [\pi \times (\text{major axis of particle} + \text{minor axis of particle})]/[2 \times \text{circumference of particle}]$$

Specific Surface Area [m²/g] of Core Particles

A sample was placed in a measurement cell, and it was then dried using a vacuum drier (VacPrep061; manufactured by Shimadzu Corporation) at 105° C. for 3 hours so as to remove moisture. Thereafter, the measurement cell was filled with nitrogen gas, it was then equipped in a specific surface area automatic measurement apparatus (Tristar3000; manufactured by Shimadzu Corporation), and the specific surface area was then measured by a BET multipoint method.

The measurement was repeatedly carried out three times, and a mean value was then obtained.

Amount of Water Vapor Adsorbed on Core Particles

A sample was dried with a vacuum drier at 105° C. for 3 hours, and approximately 30 mg of the sample was then placed in a dynamic water vapor adsorption measurement apparatus (DVS-1 type; manufactured by Surface Measurement System Ltd.). Relative humidity was set at 0% RH, and the sample was then dried at 25° C. under nitrogen current until the particle mass sufficiently reached equilibrium (mass fluctuation: 0.02%/min or less). Thereafter, relative humidity was set at 5% RH, and the sample was left until the particle mass reached equilibrium (mass fluctuation: 0.02%/min or less). Subsequently, relative humidity was set at 10% RH, and the sample was left until the particle mass reached equilibration (mass fluctuation: 0.02%/min or less). Likewise, the humidity was changed by 5% RH each, up to 15% RH, 20% RH, 25% RH, 30% RH, and 35% RH. A difference between the particle mass at a relative humidity of 30% RH and the particle mass at a relative humidity of 0% RH was obtained.

The measurement was repeatedly carried out three times, and a mean value was then obtained.

Aggregation Rate [Mass %] of Layered, Film-Coated Granules

After layering and coating operations had been performed, total quantities of recovered granules were sieved with a hand, using a JIS standard sieve with a determined opening. The mass of granules remaining on the sieve was measured. A mass percentage obtained by dividing the obtained value by the total quantities of recovered granules was defined as an aggregation rate.

$$\text{Aggregation rate [mass \%]} = (\text{mass of granules remaining on sieve}/\text{mass of recovered granules}) \times 100$$

Dissolution Rate [Mass %] of Film-Coated Granules

Using an automatic dissolution tester (DT-610; manufactured by JASCO Corporation), a drug dissolution rate was measured in accordance with the Japanese Pharmacopoeia, 15th Edition, the test method, the second method (test medium: 900 mL per medium; paddle speed: 100 rpm), and a spectrophotometer (V-530; JASCO Corporation) fixed wavelength measurement method.

Ratio [%] of Drug Content in Orally-Disintegrating Tablet with Respect to Theoretical Content Approximately 0.8 g of film-coated granules to be used in tableting was accurately weighed, and it was then sufficiently ground in a mortar. The resultant was placed in 1 L of a first solution, and it was then stirred with a stirrer for 24 hours. Thereafter, the content of a drug in the coated granules was measured using a spectrophotometer. Subsequently, based on the ratio of the content of a drug in the coated granules to coated granules mixed into an orally-disintegrating tablet, the theoretical content of the drug in the orally-disintegrating tablet was obtained. This drug content was defined as 100%.

Subsequently, the orally-disintegrating tablet obtained as a result of tableting was added to 100 mL of a first solution, and it was then stirred with a stirrer for 24 hours. Thereafter, the content of a drug in the orally-disintegrating tablet was measured, and the ratio [%] of the obtained drug content to the theoretical content was obtained as a mean value of n=10.

Drug Content CV Value [%] in Tablet

The CV value of the drug content was calculated according to the following formula (n=10):

$$CV \text{ value of drug content} = [\text{standard deviation of drug content}]/[\text{mean value of drug content}] \times 100$$

I. Production of Core Particles

Example 1

1.5 kg of microcrystalline cellulose (mean degree of polymerization: 250) was added to a high-speed stirring granulator (VG-01; manufactured by Powrex Corporation), and 900 g of distilled water was also added thereto. The mixture was blended for 30 minutes. Thereafter, 2.4 kg of the obtained wet granules was added to a rotating and fluidized bed-type granulation coating apparatus (MP-01; manufactured by Powrex Corporation). While supplying 450 g of distilled water at a rate of 7.8 g/min, the mixture was rotated at an air-supplying temperature of 25° C. for 60 minutes, and thereafter, the resultant was further rotated for 30 minutes. Thereafter, the air-supplying temperature was increased to 100° C., so as to dry the resultant. After completion of the drying, the resultant was sieved using a sieve with an opening of 106 μm and a sieve with an opening of 53 μm, and as a result, a fraction from 53 μm to 106 μm was obtained as core particles (A). The physical properties of the obtained core particles (A) are shown in Table 1.

Example 2

1.5 kg of microcrystalline cellulose (mean degree of polymerization: 250) was added to a high-speed stirring granulator, and 750 g of distilled water was also added thereto. The mixture was blended for 30 minutes. Thereafter, 2.25 kg of the obtained wet granules was added to a rotating and fluidized bed-type coating apparatus. While supplying 675 g of distilled water at a rate of 7.8 g/min, the mixture, was rotated at an air-supplying temperature of 25° C. for 90 minutes, and thereafter, the resultant was further rotated for 30 minutes. Thereafter, the air-supplying temperature was increased to 100° C., so as to dry the resultant. After completion of the drying, the resultant was sieved using a sieve with an opening of 125 μm and a sieve with an opening of 63 μm, and as a result, a fraction from 63 μm to 125 μm was obtained as core particles (B). The physical properties of the obtained core particles (B) are shown in Table 1.

Example 3

1.5 kg of microcrystalline cellulose (mean degree of polymerization: 250) was added to a high-speed stirring granulator, and 900 g of distilled water was also added thereto. The mixture was blended for 30 minutes. Thereafter, 2.4 kg of the obtained wet granules was added to a rotating and fluidized bed-type coating apparatus. While supplying 340 g of distilled water at a rate of 7.8 g/min, the mixture was rotated at an air-supplying temperature of 25° C. for 45 minutes, and thereafter, the resultant was further rotated for 30 minutes. Thereafter, the air-supplying temperature was increased to 100° C., so as to dry the resultant. After completion of the drying, the resultant was sieved using a sieve with an opening of 75 μm and a sieve with an opening of 45 μm, and as a result, a fraction from 45 μm to 75 μm was obtained as core particles (C). The physical properties of the obtained core particles (C) are shown in Table 1.

Comparative Example 1

Particles were prepared in accordance with Example 1 of the pamphlet of International Publication WO02/36168.

Commercially available KP pulp was chipped, and it was then hydrolyzed in a 10% hydrochloric acid aqueous solution at 105° C. for 30 minutes. The obtained acid-insoluble residue was filtrated and washed, so as to obtain a cake-like product of microcrystalline cellulose with a solid concentration of approximately 40%. The degree of polymerization of this cake-like product was found to be 153. This cake-like product was ground for 1 hour using all-purpose mixer-stirrer (type 5DM-03-R; manufactured by Sanei Seisakusyo, Ltd.). Water was added to the thus ground cake-like product, and the mixture was then converted to a cellulose dispersion having a solid content of 12.5 mass % using a homomixer (T. K. homomixer, type MARK2II; manufactured by Tokushu Kika Kogyo Co., Ltd.). The particle diameter, pH, and IC were adjusted, and thereafter, using a rotation board of a size of approximately 8 cm, the resultant was subjected to spray drying under conditions including a rotation number of the rotation board of approximately 5000 rpm, a flow rate of approximately 6 L/hour, an inlet air temperature of approximately 170° C., and an outlet air temperature of approximately 85° C. Thereafter, crude particles were removed using a sieve with an opening of 177 μm, and fine particles were then removed using a sieve with an opening of 45 μm, so as to obtain particles (d). The particles (d) were further sieved using a sieve with an opening of 106 μm to remove particles of 106 μm or more, so as to obtain particles (D) having a mean particle diameter of 79 μm. The physical properties of the particles (D) are shown in Table 1.

Comparative Example 2

Particles (d) were obtained in the same manner as that of Comparative Example 1. The obtained particles (d) were sieved using a sieve with an opening of 125 μm and a sieve with an opening of 45 μm to obtain a fraction from 45 μm to 125 μm, thereby obtaining particles (E) having a mean particle diameter of 97 μm. The physical properties of the particles (E) are shown in Table 1.

Comparative Example 3

Particles were prepared in the same manner as that of Example 1 of Japanese Patent No. 2542122 with the exception that the additive amount of water was decreased.

1.5 kg of microcrystalline cellulose (mean degree of polymerization: 220) was added to a high-speed stirring granulator (FS-10; manufactured by Fukae Powtex Co., Ltd.), and 1.1 kg of distilled water was also added thereto. The mixture was blended for 5 minutes. Thereafter, 500 g of the wet granules was transferred into Marumerizer Q-230 (manufactured by Fuji Paudal Co., Ltd.), and it was then rotated at 500 rpm for 10 minutes for spheronization. At the same time, 200 g of distilled water was supplied thereto at a rate of 10 g/min. Thereafter, the resultant was left at 40° C. over day and night, so that it was dried. After completion of the drying, the resultant was sieved using a sieve with an opening of 212 μm and a sieve with an opening of 106 μm to obtain a fraction from 106 μm to 212 μm, so as to obtain particles (F) having a mean particle diameter of 156 μm. The physical properties of the particles (F) are shown in Table 1.

Comparative Example 4

Particles were prepared in the same manner as that of Comparative Example 3 with the exception that the additive amount of water was decreased in comparison with Comparative Example 3.

1.5 kg of microcrystalline cellulose (mean degree of polymerization: 220) was added to a high-speed stirring granulator (FS-10; manufactured by Fukae Powtex Co., Ltd.), and 0.9 kg of distilled water was also added thereto. The mixture was blended for 5 minutes. Thereafter, 500 g of the wet granules was transferred into Marumerizer Q-230 (manufactured by Fuji Paudal Co., Ltd.), and it was then rotated at 500 rpm for 10 minutes for spheronization. At the same time, 150 g of distilled water was supplied thereto at a rate of 7.5 g/min. Thereafter, the resultant was left at 40° C. over day and night, so that it was dried. After completion of the drying, the resultant was sieved using a sieve with an opening of 106 μm and a sieve with an opening of 53 μm to obtain a fraction from 53 μm to 106 μm, so as to obtain particles (G) having a mean particle diameter of 81 μm. The physical properties of the particles (G) are shown in Table 1.

The tapped bulk density of the particles (G) was found to be 0.74 g/mL, and thus heavy core particles could not be obtained.

Comparative Example 5

Particles were prepared under scale-reduced conditions in accordance with Example 2 of Japanese Patent Publication No. 7-2761.

1.0 kg of microcrystalline cellulose (mean degree of polymerization: 250) was added to a rotating and fluidized bed-type coating apparatus (MP-01), and the rotation board was then rotated at 600 rpm. While supplying the air of 50° C. to 60° C. from the bottom, water was sprayed thereto at a rate of 20 g/min, so that granulation was conducted for 70 minutes. Thereafter, the spraying of water was terminated, and particles were then dried at 80° C. for 80 minutes. After completion of the drying, the resultant was sieved using a sieve with an opening of 125 μm and a sieve with an opening of 63 μm to obtain a fraction from 63 μm to 125 μm, so as to obtain particles (H) having a mean particle diameter of 95 μm. The physical properties of the particles (H) are shown in Table 1.

The tapped bulk density of the particles (H) was found to be 0.76 g/mL, and thus heavy core particles could not be obtained.

Comparative Example 6

It was attempted to prepare particles in the same manner as that of Example 1 with the exception that trehalose was added to a raw material.

1.35 kg of microcrystalline cellulose (mean degree of polymerization: 250) and 0.15 kg of trehalose (type P; distributed by Asahi Kasei Chemicals Corporation) were added to a high-speed stirring granulator, and 900 g of distilled water was also added thereto. The mixture was blended for 30 minutes. Thereafter, 2.4 kg of the obtained wet granules was added to a rotating and fluidized bed-type granulation coating apparatus (MP-01; manufactured by Powrex Corporation). While supplying 450 g of distilled water at a rate of 7.8 g/min, the mixture was rotated at an air-supplying temperature of 25° C. for 60 minutes, and thereafter, the resultant was further rotated for 30 minutes.

Thereafter, the air-supplying temperature was increased to 100° C., so as to dry the resultant. After completion of the drying, the resultant was sieved using a sieve with an opening of 106 μm. As a result, particles of 106 μm or less were not obtained. It was considered that, since trehalose was highly water-soluble, the stikiness of particles increased, and the particles thereby aggregated.

Comparative Example 7

It was attempted to prepare particles in the same manner as that of Example 1 with the exception that the additive amount of water was decreased in comparison with Comparative Example 6. 1.35 kg of microcrystalline cellulose (mean degree of polymerization: 250) and 0.15 kg of trehalose (type P; distributed by Asahi Kasei Chemicals Corporation) were added to a high-speed stirring granulator, and 700 g of distilled water was also added thereto. The mixture was blended for 30 minutes. Thereafter, 2.2 kg of the obtained wet granules was added to a rotating and fluidized bed-type granulation coating apparatus (MP-01; manufactured by Powrex Corporation). While supplying 250 g of distilled water at a rate of 4.2 g/min, the mixture was rotated at an air-supplying temperature of 25° C. for 60 minutes, and thereafter, the resultant was further rotated for 30 minutes.

Thereafter, the air-supplying temperature was increased to 100° C., so as to dry the resultant. After completion of the drying, the resultant was sieved using a sieve with an opening of 106 μm and a sieve with an opening of 53 μm. A fraction from 53 μm to 106 μm was obtained as core particles (I). The physical properties of the obtained core particles (I) are shown in Table 1.

The particles (I) had a tapped bulk density of 0.69 g/mL, and thus heavy core particles could not be obtained.

TABLE 1

| | | Ex. 1 | Ex. 2 | Ex. 3 | Com. Ex. 1 | Com. Ex. 2 | Com. Ex. 3 | Com. Ex. 4 | Com. Ex. 5 | Com. Ex. 6 |
|---|---|---|---|---|---|---|---|---|---|---|
| Particle | | A | B | C | D | E | F | G | H | I |
| Mean particle diameter | [μm] | 72 | 94 | 57 | 79 | 97 | 156 | 81 | 95 | 81 |
| Relative flow index | [—] | 9.4 | 9.9 | 8.8 | 5.4 | 6.7 | 16.2 | 8.2 | 8.9 | 9.5 |
| Specific surface area | [m$^2$/g] | 0.11 | 0.11 | 0.14 | 0.22 | 0.23 | 0.06 | 0.16 | 0.16 | 0.13 |
| Tapped bulk density | [g/mL] | 0.88 | 0.85 | 0.84 | 0.78 | 0.72 | 0.81 | 0.74 | 0.76 | 0.69 |
| Minor axis/major axis ratio | [—] | 0.771 | 0.774 | 0.711 | 0.844 | 0.804 | 0.838 | 0.790 | 0.801 | 0.808 |
| Surface smoothing shape factor | [—] | 0.949 | 0.935 | 0.931 | 0.920 | 0.889 | 0.941 | 0.912 | 0.907 | 0.931 |
| Amount of water vapor adsorbed | [%] | 2.9 | 3.0 | 3.1 | 3.0 | 3.0 | 0.8 | 2.4 | 2.8 | 2.5 |
| D50/D10 | [—] | 1.36 | 1.45 | 1.21 | 1.44 | 1.67 | 1.49 | 1.40 | 1.32 | 1.37 |

II. Production of Film-Coated Granules

Example 4

800 g of the core particles (A) of Example 1 was added to a modified Wurster column-equipped fluidized-bed granulation coating apparatus (MP-01; manufactured by Powrex Corporation). Thereafter, a drug suspension containing 10 parts by mass of riboflavin (manufactured by Mitsubishi Pharma Corporation), 2 parts by mass of hydroxypropylcellulose (type L; manufactured by Nippon Soda Co., Ltd.), and 88 parts by mass of water, was sprayed at a supplying rate of 5.0 g/min to the core particles (A) under conditions including a spray air pressure of 0.16 MPa, a spray air flow rate of 40 L/min, a protection air pressure of 0.2 MPa, an inlet air temperature of 75° C., an outlet air temperature of 35° C., and the volume of air of 32 m$^3$/h. Thus, the core particles (A) were coated with a riboflavin-containing coating layer, until 2 parts by mass of riboflavin was used with respect to 100 parts by mass of the core particles (A). The obtained granules were sieved using a sieve of 177 μm to remove aggregated particles, so as to obtain layered granules (A).

The aggregation rate was found to be 3% by mass or less, and thus the granules could be coated with a drug-containing layer with almost no aggregation.

Subsequently, 700 g of the obtained layered granules (A) was added to a modified Wurster column-equipped fluidized-bed granulation coating apparatus. A coating liquid was prepared by adding 2.6 parts by mass of triethyl citrate used as a plasticizer, 2.1 parts by mass of D-mannitol used as a dissolution controller, and 61.0 parts by mass of water (solid mass ratio: ethyl cellulose/triethyl citrate/D-mannitol=100/25/20) to 34.3 parts by mass of an ethyl cellulose water dispersion. Thereafter, the prepared coating liquid was sprayed to the layered granules (A) under conditions including a spray air pressure of 0.16 MPa, a spray air flow rate of 40 L/min, a protection air pressure of 0.2 MPa, an inlet air temperature of 75° C., an outlet air temperature of 35° C., the volume of air of 32 m$^3$/h, and a coating liquid-supplying rate of 5.0 g/min. Thus, the layered granules (A) were film coated with the coating liquid, until 15.0 parts by mass (solid content) of the coating liquid was applied to 100 parts by mass of the layered granules (A). The obtained film-coated granules were subjected to a heat treatment for 1 hour using a hot-air dryer at 80° C. (Perfect Oven PV-211; manufactured by Espec Corporation), so as to form a film. After cooling, the particles were sieved using a sieve of 212 μm to remove aggregated particles, so as to obtain film-coated granules (A). The aggregation rate was found to be 3% by mass or less, and thus the granules could be coated with almost no aggregation.

With regard to the obtained film-coated granules (A), a mean particle diameter, the ratio of particles of 125 μm or more, and the ratio of particles of 32 μm or less were obtained. The results are shown in Table 2.

In addition, sensory evaluation was performed on the obtained film-coated granules (A) in terms of sandy feeling when 1.0 g of the granules was placed in the oral cavity for approximately 10 seconds, using the index shown in Table 3. The results are shown in Table 4. The film-coated granules (A) caused completely no sandy feeling in the oral cavity.

Moreover, a dissolution test was carried out on the obtained film-coated granules (A). The dissolution rates of riboflavin after 1 and 5 hours are shown in Table 5. In the case of the film-coated granules (A), the dissolution rate after 1 hour was 38%, and the dissolution rate after 5 hours was 83%. Thus, the aforementioned granules exhibited sustained-release dissolution.

Example 5

A drug-containing coating layer was formed in the same manner as that of Example 4 with the exception that the core particles (B) of Example 2 were used, thereby obtaining layered granules (B). The aggregation rate was 3% by mass or less, and thus the drug could be laminated on the core particles with almost no aggregation.

In addition, a film coating operation was carried out in the same manner as that of Example 4 with the exception that the obtained layered granules (B) were used, thereby obtaining film-coated granules (B). The aggregation rate was 3% by mass or less, and thus the granules could be coated with almost no aggregation.

With regard to the obtained film-coated granules (B), a mean particle diameter, the ratio of particles of 125 μm or more, and the ratio of particles of 32 μm or less were obtained. The results are shown in Table 2.

In addition, sensory evaluation was performed on the obtained film-coated granules (B) in terms of sandy feeling when 1.0 g of the granules was placed in the oral cavity for approximately 10 seconds, using the index shown in Table 3. The results are shown in Table 4. The film-coated granules (B) caused almost no sandy feeling in the oral cavity.

Moreover, a dissolution test was carried out on the obtained film-coated granules (B). The dissolution rates of riboflavin after 1 and 5 hours are shown in Table 5. In the case of the film-coated granules (B), the dissolution rate after 1 hour was 27%, and the dissolution rate after 5 hours was 67%. Thus, the granules exhibited sustained-release dissolution, and the riboflavin dissolution rate of the film-coated granules (B) was slightly lower than that of the film-coated granules (A). This is because the mean particle diameter of the core particles (B) is larger than that of the core particles (A).

Example 6

A drug-containing coating layer was formed in the same manner as that of Example 4 with the exception that the core particles (C) of Example 3 were used, thereby obtaining layered granules (C). The aggregation rate was 3% by mass or less, and thus the drug could be laminated on the core particles with almost no aggregation.

In addition, a film coating operation was carried out in the same manner as that of Example 4 with the exception that the obtained layered granules (C) were used, thereby obtaining film-coated granules (C). The aggregation rate was 3% by mass or less, and thus the granules could be coated with almost no aggregation.

With regard to the obtained film-coated granules (C), a mean particle diameter, the ratio of particles of 125 μm or more, and the ratio of particles of 32 μm or less were obtained. The results are shown in Table 2.

In addition, sensory evaluation was performed on the obtained film-coated granules (C) in terms of sandy feeling when 1.0 g of the granules was placed in the oral cavity for approximately 10 seconds, using the index shown in Table 3. The results are shown in Table 4. The film-coated granules (C) caused completely no sandy feeling in the oral cavity.

Comparative Example 8

A drug-containing coating layer was formed in the same manner as that of Example 4 with the exception that the particles (D) of Comparative Example 1 were used, thereby obtaining layered granules (D). The aggregation rate was 3% by mass or less, and thus the drug could be laminated on the particles with almost no aggregation.

In addition, a film coating operation was carried out in the same manner as that of Example 4 with the exception that the obtained layered granules (D) were used, thereby obtaining film-coated granules (D). The aggregation rate was 3% by mass or less, and thus the granules could be coated with almost no aggregation.

With regard to the obtained film-coated granules (D), a mean particle diameter, the ratio of particles of 125 μm or more, and the ratio of particles of 32 μm or less were obtained. The results are shown in Table 2.

In addition, sensory evaluation was performed on the obtained film-coated granules (D) in terms of sandy feeling when 1.0 g of the granules was placed in the oral cavity for approximately 10 seconds, using the index shown in Table 3. The results are shown in Table 4. The film-coated granules (D) caused completely no sandy feeling in the oral cavity.

Moreover, a dissolution test was carried out on the obtained film-coated granules (D). The dissolution rates of riboflavin after 1 and 5 hours are shown in Table 5. In the case of the film-coated granules (D), the dissolution rate after 1 hour was 58%, and the dissolution rate after 5 hours was 94%. The dissolution rate of the film-coated granules (D) was higher than that of the film-coated granules (A) having a mean particle diameter smaller than that of the film-coated granules (D). Thus, the dissolution of riboflavin could not be sufficiently suppressed. In order to achieve the same dissolution rate as that of the film-coated granules (A) while using the layered granules (D), 100 parts by mass of the layered granules (D) should have been coated with 20.0 parts by mass (solid content) of the coating liquid.

Comparative Example 9

A drug-containing coating layer was formed in the same manner as that of Example 4 with the exception that the particles (E) of Comparative Example 2 were used, thereby obtaining layered granules (E). The aggregation rate was 3% by mass or less, and thus the drug could be laminated on the particles with almost no aggregation.

In addition, a film coating operation was carried out in the same manner as that of Example 4 with the exception that the obtained layered granules (E) were used, thereby obtaining film-coated granules (E). The aggregation rate was 3% by mass or less, and thus the granules could be coated with almost no aggregation.

With regard to the obtained film-coated granules (E), a mean particle diameter, the ratio of particles of 125 μm or more, and the ratio of particles of 32 μm or less were obtained. The results are shown in Table 2.

In addition, sensory evaluation was performed on the obtained film-coated granules (E) in terms of sandy feeling when 1.0 g of the granules was placed in the oral cavity for approximately 10 seconds, using the index shown in Table 3. The results are shown in Table 4. The film-coated granules (E) caused almost no sandy feeling in the oral cavity.

Moreover, a dissolution test was carried out on the obtained film-coated granules (E). The dissolution rates of riboflavin after 1 and 5 hours are shown in Table 5. In the case of the film-coated granules (E), the dissolution rate after 1 hour was 42%, and the dissolution rate after 5 hours was 94%. The dissolution rate of the film-coated granules (E) was higher than the film-coated granules (A) and (B) each having a mean particle diameter smaller than that of the film-coated granules (E). Thus, the dissolution of riboflavin could not be sufficiently suppressed.

Comparative Example 10

A drug-containing coating layer was formed in the same manner as that of Example 4, with the exception that the particles (F) of Comparative Example 2 were used, and that a sieve of 250 μm was used to remove aggregated particles from the obtained granules, thereby obtaining layered granules (F). The aggregation rate was 3% by mass or less, and thus the drug could be laminated on the particles with almost no aggregation.

In addition, a film coating operation was carried out in the same manner as that of Example 4 with the exception that the obtained layered granules (F) were used, and that a sieve of 250 μm was used to remove aggregated particles from the obtained granules, thereby obtaining film-coated granules (F). The aggregation rate was 3% by mass or less, and thus the granules could be coated with almost no aggregation.

With regard to the obtained film-coated granules (F), a mean particle diameter, the ratio of particles of 125 μm or more, and the ratio of particles of 32 μm or less were obtained. The results are shown in Table 2.

In addition, sensory evaluation was performed on the obtained film-coated granules (F) in terms of sandy feeling when 1.0 g of the granules was placed in the oral cavity for approximately 10 seconds, using the index shown in Table 3. The results are shown in Table 4. As a result, the film-coated granules (F) caused sandy feeling in the oral cavity.

Comparative Example 11

A drug-containing coating layer was formed in the same manner as that of Example 4, with the exception that the particles (H) of Comparative Example 5 were used, and that a sieve of 250 μm was used to remove aggregated particles from the obtained granules, thereby obtaining layered granules (H). The aggregation rate was 3% by mass or less, and thus the drug could be laminated on the particles with almost no aggregation.

In addition, a film coating operation was carried out in the same manner as that of Example 4, with the exception that the obtained layered granules (H) were used, and that a sieve of 250 μm was used to remove aggregated particles from the obtained granules, thereby obtaining film-coated granules (H). The aggregation rate was 3% by mass or less, and thus the granules could be coated with almost no aggregation.

With regard to the obtained film-coated granules (H), a mean particle diameter, the ratio of particles of 125 μm or more, and the ratio of particles of 32 μm or less were obtained. The results are shown in Table 2.

In addition, sensory evaluation was performed on the obtained film-coated granules (H) in terms of sandy feeling when 1.0 g of the granules was placed in the oral cavity for approximately 10 seconds, using the index shown in Table 3. The results are shown in Table 4. The film-coated granules (H) caused almost no sandy feeling in the oral cavity.

Moreover, a dissolution test was carried out on the obtained film-coated granules (H). The dissolution rates of riboflavin after 1 and 5 hours are shown in Table 5. In the case of the film-coated granules (H), the dissolution rate after 1 hour was 39%, and the dissolution rate after 5 hours was 89%. The dissolution rate of the film-coated granules (H) was higher than the film-coated granules (A) and (B) each having a mean particle diameter smaller than that of the film-coated granules (H). Thus, the dissolution of riboflavin could not be sufficiently suppressed.

Comparative Example 12

A drug-containing coating layer was formed in the same manner as that of Example 4 with the exception that the particles (I) of Comparative Example 7 were used, thereby obtaining layered granules (I). The aggregation rate was 45% by mass, and thus a large amount of aggregate was generated as a result of the drug coating. This was considered because aggregation easily occurred due to a low tapped bulk density or generation of stikiness due to the water-solubility of trehalose, in comparison with the particles (A) of Example 1.

TABLE 2

|  |  | Ex. 4 | Ex. 5 | Ex. 6 | Com. Ex. 8 | Com. Ex. 9 | Com. Ex. 10 | Com. Ex. 11 | Com. Ex. 12 |
|---|---|---|---|---|---|---|---|---|---|
| Film-coated granules | | A | B | C | D | E | F | H | I |
| Mean particle diameter | [μm] | 76 | 97 | 61 | 82 | 101 | 159 | 98 | Occurrence of aggregation |
| Ratio of particles of 125 μm or more | [%] | 1.7 | 4.3 | 0.3 | 1.4 | 3.7 | 76.1 | 4.8 | |
| Ratio of particles of 32 μm or less | [%] | 1.3 | 0.8 | 1.1 | 1.6 | 0.7 | 0.1 | 0.3 | |

TABLE 3

| ◎ | Completely no sandy feeling felt |
|---|---|
| ○ | Almost no sandy feeling felt |
| X | Sandy feeling felt |

TABLE 4

|  | Ex. 4 | Ex. 5 | Ex. 6 | Com. Ex. 8 | Com. Ex. 9 | Com. Ex. 10 | Com. Ex. 11 |
|---|---|---|---|---|---|---|---|
| Film-coated granules | A | B | C | D | E | F | H |
| Sandy feeling | ◎ | ○ | ◎ | ◎ | ○ | X | ○ |

TABLE 5

|  |  | Ex. 4 | Com. Ex. 6 | Ex. 5 | Com. Ex. 9 | Com. Ex. 11 |
|---|---|---|---|---|---|---|
| Film-coated granules | | A | D | B | E | H |
| Granule diameter | [μm] | 76 | 82 | 97 | 101 | 103 |
| Dissolution rate after 1 hour | [%] | 38 | 58 | 27 | 42 | 39 |
| Dissolution rate after 5 hours | [%] | 83 | 94 | 67 | 94 | 88 |

III. Production of Tablets

Example 7

150 g of the film-coated granules (A) obtained in Example 4, 100 g of microcrystalline cellulose "Ceolus KG-802" (manufactured by Asahi Kasei Chemicals Corporation), 100 g of low-substituted hydroxypropylcellulose "L-HPC LH-B1" (manufactured by Shin-Etsu Chemical Co., Ltd.), 700 g of granulated mannitol "PEARLITOL 200SD" (manufactured by ROQUETTE), 45 g of a disintegrator "Kiccolate" (distributed by Asahi Kasei Chemicals Corporation), and 5 g of magnesium stearate used as a lubricant (Taihei Chemical Industrial Co., Ltd.) were placed in a PE bag, and they were then mixed with hands for 3 minutes, so as to obtain powders to be used in tableting. Thereafter, the powders to be used in tableting were filled in a hopper, and a rotary tableting machine (Clean Press Collect 12HUK; manufactured by Kikusui Seisakusho Co., Ltd.) was then used to produce R tablets (8 mφ, 180 mg) under conditions including a tableting rate of 54 rpm and a compression pressure of 6 kN. Such tableting was carried out for 8 minutes, until the powders to be used in tableting were not supplied from the hopper. The produced tablets were sampled 1, 4, and 7 minutes after initiation of the tableting. The drug content in the tablet and a CV value were measured. The results are shown in Table 6.

With regard to the obtained tablets, the drug content in the tablets was close to the theoretical value (100%), and a deviation of such content was small, regardless of the tableting time.

The hardness of the tablets sampled 4 minutes after initiation of the tableting, and the disintegration time of the tablets in the oral cavity are shown in Table 6.

The obtained tablets had sufficient hardness. On the other hand, the disintegration time of the tablets in the oral cavity was extremely short, and thus these tablets could be consumed without water. In addition, these tablets caused almost no sandy feeling in the oral cavity.

Comparative Example 13

Orally-disintegrating tablets were produced under the same conditions as those of Example 7 with the exception that the film-coated granules (F) of Comparative Example 8 were used. Tableting was also carried out for 8 minutes, until the powders to be used in tableting were not supplied from the hopper. The produced tablets were sampled 1, 4, and 7 minutes after initiation of the tableting. The drug content in the tablet and a CV value were measured. The results are shown in Table 6.

With regard to the obtained tablets, the drug content in the tablets was high immediately after initiation of the tableting. However, there was a phenomenon whereby the drug content was decreased as the tableting time was proceeded. In addition, a deviation of such drug content was greater than that of Example 7. This was considered because the film-coated granules (F) were separated and segregated from the powders of additives used in the tableting, and thus because the film-coated granules (F), which had high fluidity, were first supplied from the hopper.

Moreover, the hardness of the tablets sampled 4 minutes after initiation of the tableting, and the disintegration time of the tablets in the oral cavity are shown in Table 6. The tablets had sufficient hardness, and the disintegration time of the tablets in the oral cavity was short. However, these tablets caused sandy feeling in the oral cavity, and thus it was difficult to consume the tablets without water.

TABLE 6

| | | Ex. 7 | | | Com. Ex. 13 | | |
|---|---|---|---|---|---|---|---|
| | | Film-coated granules | | | | | |
| | | A | | | F | | |
| | | After 1 minute | After 4 minutes | After 7 minutes | After 1 minute | After 4 minutes | After 7 minutes |
| Mean drug content | [%] | 101.5 | 99.1 | 100.4 | 103.4 | 98.7 | 96.7 |
| CV value | [%] | 1.02 | 0.88 | 0.97 | 2.11 | 1.98 | 2.35 |
| Tablet hardness | [N] | | 61 | | | 54 | |
| Disintegration time | [sec] | | 35 | | | 33 | |
| Sandy feeling in oral cavity | | | No | | | Yes | |

The present application is based on a Japanese Patent Application (Japanese Patent Application No. 2007-150003) filed to the Japan Patent Office on Jun. 6, 2007, and the disclosures thereof are incorporated herein by reference.

INDUSTRIAL APPLICABILITY

The core particle of the present invention can preferably be used in the production of various types of granules.

In particular, the core particle of the present invention is suitable for the production of a layered granule using an aqueous drug suspension or the production of a coated granule using an aqueous coating liquid.

Moreover, the core particle of the present invention can preferably be used in the field of a granule having a medicinal ingredient-containing coating layer, a film-coated granule produced by further coating this granule with a film, and a capsule and a granule-containing tablet produced using the film-coated granule.

The invention claimed is:

1. A core particle, which comprises more than 95% by mass of microcrystalline cellulose, and which has
    a mean particle diameter of less than 100 µm,
    a relative flow index of 7.0 to 30.0,
    a specific surface area of less than 0.15 m²/g, and
    a tapped bulk density of 0.80 g/mL or more.

2. The core particle according to claim 1, wherein the mean particle diameter is from 10 µm to less than 100 µm.

3. The core particle according to claim 1, wherein the mean particle diameter is from 50 µm to less than 100 µm.

4. The core particle according to claim 1, wherein the relative flow index is 7.0 to 15.0.

5. The core particle according to claim 1, wherein a major axis/a minor axis ratio thereof is 0.7 or greater, and a surface smoothing shape factor thereof is 0.925 or greater.

6. The core particle according to claim 1, wherein the amount of water vapor adsorbed is 1.50% or more.

7. A granule, which comprises a core particle according to claim 1 and a coating layer that coats the core particle.

8. A film-coated granule, which comprises a granule according to claim 7 and
    a film coating layer that coats the granule.

9. A tablet comprising the film-coated granule according to claim 8.

10. A capsule comprising a film-coated granule according to claim 8.

11. The tablet according to claim 9, which is an orally-disintegrating tablet.

12. The capsule according to claim 10, which is an orally-disintegrating tablet.

13. A process for producing the core particle of claim 1, which comprises the steps of:
    granulating a particle by stirring and mixing microcrystalline cellulose and a binder liquid; and
    spraying a binder liquid to the particle obtained in the previous step, while allowing the particle to flow by a stream of air and also rotating the particle.

* * * * *